(12) United States Patent
Lisogurski

(10) Patent No.: US 8,929,963 B2
(45) Date of Patent: Jan. 6, 2015

(54) DEVICES AND METHODS FOR REDUCING WIRELESS COMMUNICATION IN A PATIENT MONITORING SYSTEM

(75) Inventor: Daniel Lisogurski, Boulder, CO (US)

(73) Assignee: Covidien LP, Mansfield, MA (US)

( * ) Notice: Subject to any disclaimer, the term of this patent is extended or adjusted under 35 U.S.C. 154(b) by 792 days.

(21) Appl. No.: 13/182,643

(22) Filed: Jul. 14, 2011

(65) Prior Publication Data

US 2013/0018239 A1 Jan. 17, 2013

(51) Int. Cl.
*A61B 5/1455* (2006.01)
*A61B 5/00* (2006.01)
(Continued)

(52) U.S. Cl.
CPC ........... *A61B 5/14551* (2013.01); *A61B 5/0004* (2013.01); *A61B 5/02416* (2013.01);
(Continued)

(58) Field of Classification Search
USPC .......... 600/310, 322, 323, 336, 300; 128/903; 340/573.1
See application file for complete search history.

(56) References Cited

U.S. PATENT DOCUMENTS 4,911,167 A 3/1990 Corenman et al.
5,919,141 A 7/1999 Money et al.
(Continued)

FOREIGN PATENT DOCUMENTS

DE 19632361 2/1997
EP 0127947 12/1984
(Continued)

OTHER PUBLICATIONS

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.
(Continued)

*Primary Examiner* — Eric Winakur
(74) *Attorney, Agent, or Firm* — Fletcher Yoder PC

(57) ABSTRACT

The present disclosure relates generally to patient monitoring systems and, more particularly, to wireless patient sensors and patient monitors. In an embodiment, a patient sensor device includes an emitter configured to emit light into a tissue of a patient as well as a detector configured to detect the light from the tissue of the patient and produce a corresponding electrical signal. The patient sensor also includes signal processing circuitry configured to receive and convert the electrical signal of the detector into detector signal data. The patient sensor also includes a wireless module communicatively coupled to a patient monitor and configured to transmit a physiological parameter value, the detector signal data, or both, to the patient monitor. The patient sensor also includes a processor configured to determine whether the patient sensor or the patient monitor should calculate the physiological parameter value based, at least in part, on the detector signal data. The processor is also configured to calculate the physiological parameter value for the patient based, at least in part, on the detector signal data, if the processor determines that the patient sensor should calculate the physiological parameter value. The processor is also configured to send the detector signal data to the patient monitor, via the wireless module, to calculate the physiological parameter value for the patient based, at least in part, on the detector signal data, if the processor determines that the patient monitor should calculate the physiological parameter value.

20 Claims, 6 Drawing Sheets

(51) Int. Cl.
*A61B 5/024* (2006.01)
*G06F 19/00* (2011.01)
*A61B 5/0205* (2006.01)
*A61B 5/021* (2006.01)
*A61B 5/0402* (2006.01)
*A61B 5/08* (2006.01)

(52) U.S. Cl.
CPC ............ *A61B 5/6826* (2013.01); *A61B 5/7203* (2013.01); *A61B 5/7221* (2013.01); *A61B 5/7271* (2013.01); *G06F 19/3418* (2013.01); *A61B 2560/0209* (2013.01); *A61B 5/02055* (2013.01); *A61B 5/021* (2013.01); *A61B 5/0402* (2013.01); *A61B 5/0816* (2013.01); *Y10S 128/903* (2013.01)
USPC ........................... 600/310; 600/336; 128/903

(56) References Cited

U.S. PATENT DOCUMENTS

| | | | |
|---|---|---|---|
| 6,035,223 A * | 3/2000 | Baker, Jr. ................. | 600/323 |
| 6,411,833 B1 | 6/2002 | Baker, Jr. et al. | |
| 7,209,775 B2 | 4/2007 | Bae et al. | |
| 2005/0113655 A1 | 5/2005 | Hull | |
| 2005/0148882 A1 | 7/2005 | Banet et al. | |
| 2005/0228244 A1 | 10/2005 | Banet | |
| 2006/0122520 A1 | 6/2006 | Banet et al. | |
| 2006/0253007 A1 | 11/2006 | Cheng et al. | |
| 2006/0276714 A1 | 12/2006 | Holt et al. | |
| 2006/0287589 A1 | 12/2006 | Wobermin et al. | |
| 2008/0021287 A1 | 1/2008 | Woellenstein et al. | |
| 2009/0240125 A1 | 9/2009 | Such et al. | |
| 2009/0247849 A1 | 10/2009 | McMutcheon et al. | |
| 2011/0034783 A1 | 2/2011 | Lisogurski et al. | |

FOREIGN PATENT DOCUMENTS

| | | |
|---|---|---|
| FR | 2685865 | 7/1993 |
| JP | 6154177 | 6/1994 |
| JP | 25169020 A2 | 6/2005 |
| JP | 4038280 B2 | 1/2008 |
| JP | 28161657 A2 | 7/2008 |
| WO | WO9309711 | 5/1993 |
| WO | WO9502358 | 1/1995 |
| WO | 0157877 A1 | 8/2001 |
| WO | WO02062213 | 8/2002 |

OTHER PUBLICATIONS

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Such, Hans Olaf; "Optoelectronic Non-invasive Vascular Diagnostics Using multiple Wavelength and Imaging Approach," *Dissertation*, (1998).

Ferrell, T.L., et al.; "Medical Telesensors," *SPIE*, vol. 3253, pp. 193-198 (1998).

Ikeda, Kenji, et al.; "Improvement of Photo-Electric Plethysmograph Applying Newly Developed Opto-Electronic Devices," *IEEE Tencon*, pp. 1109-1112 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Aoyagi, T., et al.; "Pulse Oximeters: background, present and future," *Neonatal Care*, vol. 13, No. 7, pp. 21-27 (2000) (Article in Japanese—contains English summary of article).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Lopez-Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Shaltis, Phillip, et al.; "Implementation and Validation of a Power-Efficient, High-Speed Modulation Design for Wireless Oxygen Saturation Measurement Systems," IEEE, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Aoyagi, Takuo; "Pulse oximetry: its invention, theory, and future," *Journal of Anesthesia*, vol. 17, pp. 259-266 (2003).

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003.

Itoh, K., et al.; "Pulse Oximeter," *Toyaku Zasshi* (Toyaku Journal), vol. 25, No. 8, pp. 50-54 (2003) (Article in Japanese—contains English summary of article).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Pujary, C., et al.; "Photodetector Size Considerations in the Design of a Noninvasive Reflectance Pulse Oximeter for Telemedicine Applications," IEEE, pp. 148-149 (2003).

Wendelken, Suzanne, et al.; "The Feasibility of Using a Forehead Reflectance Pulse Oximeter for Automated Remote Triage," IEEE, pp. 180-181 (2004).

Johnston, William S., et al.; "Effects of Motion Artifacts on helmet-Mounted Pulse Oximeter Sensors," pp. 214-215 (2004).

Matsuzawa, Y., et al.; "Pulse Oximeter," *Home Care Medicine*, pp. 42-45 (Jul. 2004); (Article in Japanese—contains English summary of article).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

(56) References Cited

OTHER PUBLICATIONS

Odagiri, Y.; "Pulse Wave Measuring Device," *Micromechatronics*, vol. 42, No. 3, pp. 6-11 (undated) (Article in Japanese—contains English summary of article).

Johnston; "Investigation of Signal Processing Algorithms for an Embedded Microcontroller-Based Wearable Pulse Oximeter,"Proceedings of the 28th IEEE EMBS, Annual International Conference, New York City, NY USA, SaEP5.3, pp. 5888-5891 (Aug. 30-Sep. 3, 2006).

International Search Report and Written Report for PCT No. PCT/US2012/042138 dated Sep. 10, 2012; 11 pages.

* cited by examiner

US 8,929,963 B2

DEVICES AND METHODS FOR REDUCING WIRELESS COMMUNICATION IN A PATIENT MONITORING SYSTEM

BACKGROUND

The present disclosure relates generally to wireless patient monitoring systems and, more particularly, to wireless patient sensors and patient monitors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Patient sensors are used in a variety of medical applications to determine physiological parameters of a patient. For example, a pulse oximetry sensor may perform measurements such that a patient's pulse rate and/or blood oxygen saturation may be determined. Such patient sensors may communicate with a patient monitor using a communication cable. For example, a patient sensor may use such a communication cable to send a signal, corresponding to a measurement performed by the sensor, to the patient monitor for processing. However, the use of communication cables may limit the range of applications available, as the cables may become prohibitively expensive at long distances as well as limit a patient's range of motion by physically tethering the patient to a monitoring device.

Although wireless patient sensors may transmit information without the need for a communication cable, wireless patient sensors typically employ batteries to power the device. Since batteries afford a limited power source, wireless patient sensors may only be operational for a limited window of time before the battery is depleted and must be recharged or replaced to continue sensor operation. Furthermore, wireless devices may be prevalent in some medical environments, which may result in congestion or interference during wireless communication.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
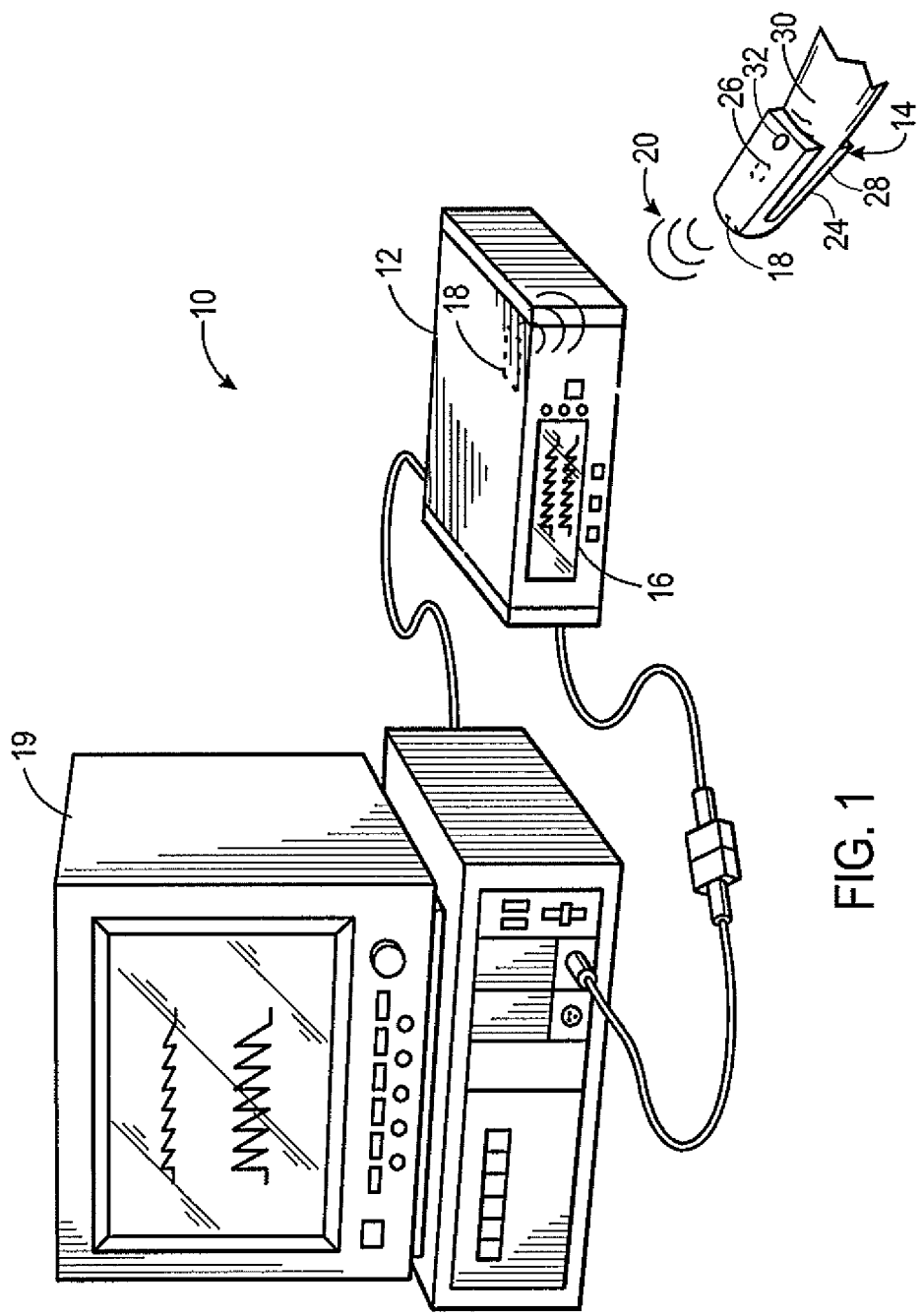
FIG. 1 is a perspective view of a patient sensor system, in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In certain circumstances, it may be desirable for a wireless patient sensor to perform measurements on a patient as well as to calculate a physiological parameter of the patient. For example, as described above, it may be desirable to minimize power consumption in a wireless patient sensor to maximize the operational time of the sensor before its battery is depleted and must be recharged or replaced. Furthermore, with the number of wireless devices being used in medical environments steadily increasing, it may also be desirable for wireless medical devices communicate as little as possible in order to minimize interference and congestion in the wireless spectrum.

With the foregoing in mind, previously described wireless patient sensors generally lacked adequate processing circuitry for complex algorithms and, therefore, performed little or no signal processing at the sensor. Accordingly, such a sensor would transmit all of the detector signal data to a patient monitor for processing, and this continual transmission of data would quickly discharge the battery of the sensor and create a significant amount of wireless traffic. To address these issues, the present embodiments describe a wireless patient sensor that is equipped with a low-power processor and memory to enable the calculation of the physiological parameter at the sensor. In the disclosed embodiments, the patient sensor may, in general, fully process the detector signal and only send the calculated value for the physiological parameter to the patient monitor, which represents significantly less wireless data transmission. Additionally, in certain embodiments, the calculated value for the physiological parameter may only be sent to the monitor when there is a change in the value, thereby further reducing wireless communication. Since less battery power may be consumed by the sensor for wireless communication, the disclosed embodiments may effectively improve battery conservation in the sensor while reducing wireless network congestion.

For example, in a given 24 hour period a patient may only be active (e.g., walking, moving, eating, etc.) for limited periods of time. As such, a large portion of a patient's time may involve little movement or activity, such as when the patient is sleeping or resting. This means that, for a substantial portion of the patient's time, the lack of movement by the patient, and potentially the low ambient lighting, may allow a patient sensor to make physiological data measurements having little to no signal artifacts. Accordingly, the disclosed embodiments afford the greatest advantage (e.g., in terms of battery savings) under such circumstances.

However, since the disclosed patient sensor embodiments are equipped with a low-power processor and memory, the sensor may be effectively limited to calculating the physiological parameter from relatively simple detector signals. That is, if the detector signal becomes too noisy or too complex, the low-power processor and memory of the patient sensor may lack sufficient processing power to employ more complex algorithms to accurately calculate the physiological parameter. In such circumstances, it may be beneficial to instead have the patient monitor perform the calculation of the physiological parameter. That is, the patient monitor may be more apt to perform the calculation of the physiological parameter for noisy or complex detector signals since the monitor may include a more powerful processor and memory than the patient sensor. Furthermore, the patient monitor may be powered by an electrical outlet and, therefore, may not be confined by the same power limitations as a battery-powered patient sensor. Accordingly, the present disclosure describes embodiments in which the patient sensor system determines when the detector signal is sufficiently noise-free and simple for the sensor to process and when the raw detector data should be sent to the patient monitor for processing.

With the foregoing in mind, FIG. 1 illustrates a perspective view of an embodiment of a patient monitoring system 10, including a patient monitor 12 and a wireless patient sensor 14. The patient monitoring system 10 is configured to enable the calculation of one or more physiological parameters of a patient on the wireless patient sensor 14 in order to limit wireless communication and to conserve battery power in the wireless patient sensor 14. Although the illustrated embodiment of system 10 is a pulse oximetry monitoring system, it should be noted that the patent monitoring system 10 may be configured to perform any number of measurements on a patient to determine one or more physiological parameters of the patient. That is, while the pulse oximetry monitoring system 10 may determine pulse rates and blood oxygen saturation levels (e.g., $SpO_2$ values) for a patient, the system 10 may, additionally or alternatively, be configured to determine a patient's respiration rate, glucose levels, hemoglobin levels, hematocrit levels, tissue hydration, as well as other physiological parameters.

The patient monitor 12 of the patient monitoring system 10 communicates wirelessly with the wireless patient sensor 14. The patient monitor 12 may include a display 16, a wireless module 18 for transmitting and receiving wireless data, a memory, a processor, and various monitoring and control features. Based on data received from the wireless medical sensor 14, the patient monitor 12 may display physiological parameters of the patient on display 16. In certain embodiments, the physiological parameter of the patient may be calculated by the wireless patient sensor 14. However, as discussed in detail below, in certain embodiments the patient monitor 12 may calculate the physiological parameter instead of, or in addition to, the patient sensor 14, depending on the noise level and complexity of the detector signal. The system 10 may also be communicatively coupled to a multi-parameter monitor 19 to facilitate presentation of patient data, such as pulse oximetry data determined by system 10 and/or physiological parameters determined by other patient monitoring systems (e.g., electrocardiographic (ECG) monitoring system, a respiration monitoring system, a blood pressure monitoring system, etc.). For example, the multi-parameter monitor 19 may display a graph of $SpO_2$ values, a current pulse rate, a graph of blood pressure readings, an electrocardiograph, and/or other related patient data in a centralized location for quick reference by a medical professional.

In the illustrated embodiment of the patient monitoring system 10, the wireless patient sensor 14 is a pulse oximetry sensor. As should be appreciated, however, the sensor 14 may be chosen to obtain any of a variety of medical measurements, such as a respiration rate, patient temperature, ECG, blood pressure, pulse transit time, and so forth. In certain embodiments, the wireless patient sensor 14 may be completely or partially disposable. That is, in certain embodiments, a portion of the wireless patient sensor 14 may be disposed after patient use. In certain embodiments, the wireless patient sensor 14 may be constructed in a modular fashion such that portions of the sensor 14 (e.g., processing circuitry) may be removed to be recycled into other sensors while other portions (e.g., the body) of the sensor 14 are disposed.

Like the patient monitor 12, the patient sensor 14 also includes a wireless module 18. The wireless module 18 of the sensor 14 may establish wireless communication 20 with the wireless module 18 of the patient monitor 12 using any suitable protocol. For example, the wireless modules 18 may be capable of communicating using the IEEE 802.15.4 standard, and may be, for example, ZigBee, WirelessHART, or MiWi modules. Additionally or alternatively, the wireless modules 18 may be capable of communicating using the Bluetooth standard, one or more of the IEEE 802.11 standards, an ultra-wideband (UWB) standard, or a near-field communication (NFC) standard. As described further below, the wireless module 18 of the patient sensor 14 may be used to transmit either raw detector signals or calculated physiological parameter values to the patient monitor 12 depending on the noise level and/or complexity of the detector signal. Additionally, the monitor 12 may use the wireless module 18 to send the sensor 14 instructions and/or operational parameters set by the operator using the monitor 12.

The wireless patient sensor 14, illustrated in the present embodiment as a pulse oximetry sensor 14, includes an emitter 24 and a detector 26 coupled to the body 28 of the sensor 14. The body 28 of the wireless patient sensor 14 may attach to patient tissue (e.g., a patient's finger, ear, forehead, or toe). For example, in the illustrated embodiment, the sensor 14 is configured to attach to a finger of the patient 30. When attached to pulsatile tissue, the emitter 24 may transmit light at certain wavelengths (e.g., for example, RED light and/or IR light) into the tissue, wherein the RED light may have a wavelength of about 600 to 700 nm, and the IR light may have a wavelength of about 800 to 1000 nm. The detector 26 may receive the RED and IR light after it has passed through or is reflected by the tissue. The amount of light that passes through the patient tissue and other characteristics of light waves may vary according to the changing amount of certain blood constituents in the tissue and the related light absorption and/or scattering. For example, the emitter 24 may emit light from two or more LEDs, or other suitable light sources, into the pulsatile tissue of the patient 30. The reflected or transmitted light may be detected with the detector 26, such as a photodiode or photo-detector, after the light has passed through or has been reflected by the pulsatile tissue. Additionally, the wireless patient sensor 14 may include a button or switch 32 which may be used to activate and deactivate the sensor 14.

Figure 2:
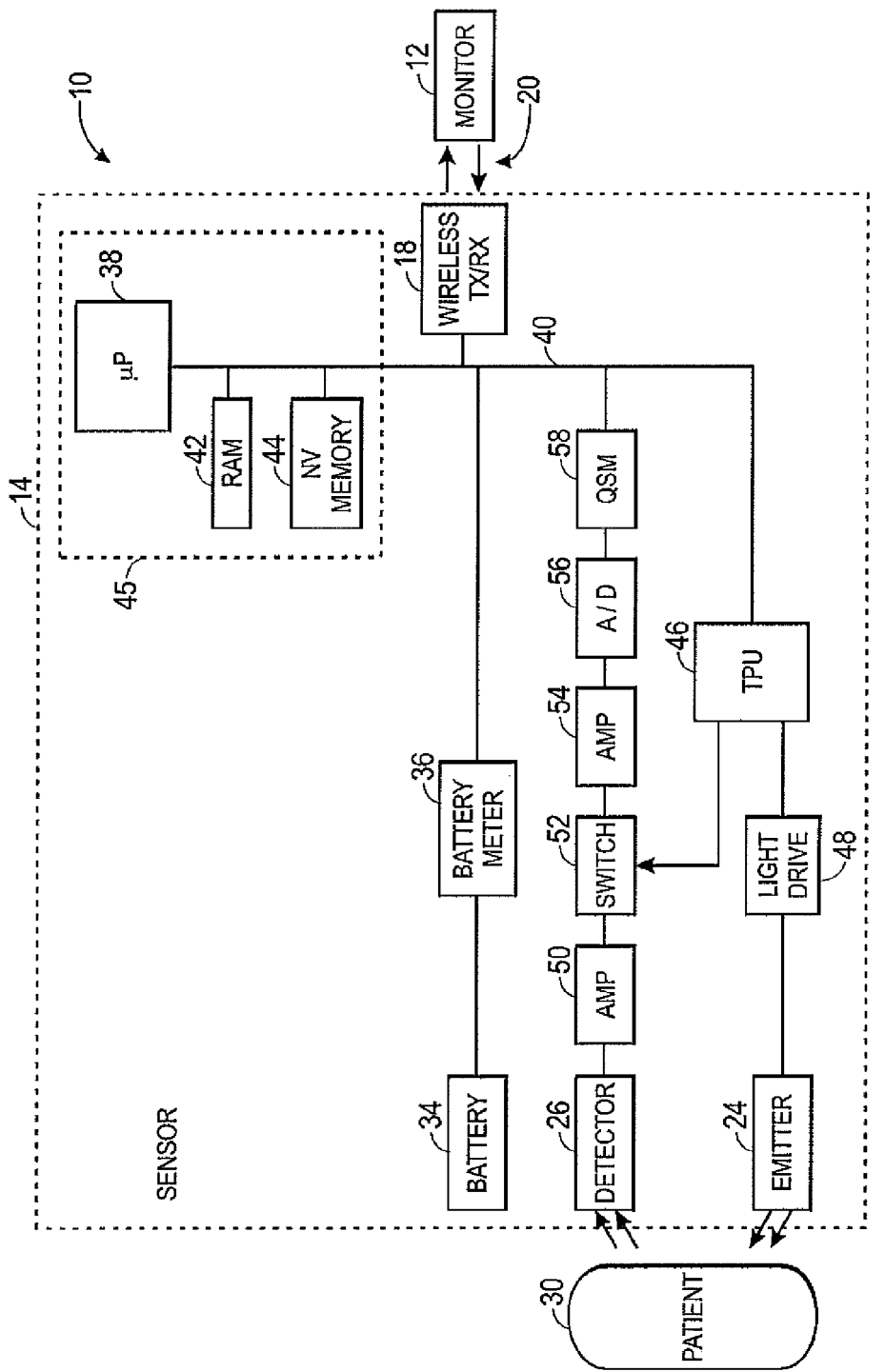
FIG. 2 is a block diagram of the wireless patient sensor of FIG. 1, in accordance with an embodiment.

As discussed above, sensor 14 may be configured to calculate of one or more physiological parameters of a patient on the wireless medical sensor 14 to minimize wireless communication of the system 10 and improve sensor efficiency. In accordance with one example, FIG. 2 illustrates a plurality of components that may be present within the body 28 of the wireless patient sensor 14 to facilitate the acquisition, processing, and transmission of physiological parameter data. The system 10 includes the patient monitor 12 and the sensor 14, which may be configured to obtain, for example, a plethysmographic signal from patient tissue at certain predetermined wavelengths. The patient sensor 14 may be communicatively connected to the patient monitor 12 via wireless communication 20. When the sensor 14 is operating, light from the emitter 24 may pass into the patient 30 and be scattered and detected by the detector 26.

A battery 34 may supply the wireless patient sensor 14 with operating power. By way of example, the battery 34 may be a rechargeable battery (e.g., a lithium ion, lithium polymer, nickel-metal hydride, or nickel-cadmium battery) or may be a single-use battery such as an alkaline or lithium battery. Since the techniques described herein are directed toward reduced battery consumption, the battery 34 may be of a lower capacity, and accordingly much smaller and/or cheaper, than a battery needed to power a similar wireless sensor that does not employ the disclosed techniques. A battery meter 36 may provide the expected remaining power of the battery 34 to the microprocessor 38.

The patient sensor 14 may also include a microprocessor 38 coupled to the main system bus 40 that controls the operation of the sensor 14. In general, the processor 38 may be a low-power processor compared to the processor that may be present within the patient monitor 12. Many suitable products exist and the selection of a device depends on many factors. For example, the processor 38 may be an 8-bit or 16-bit micro-controller such as an 8051, Microchip PIC or Texas Instruments MSP430, consuming only a few milliwatts of power. Other suitable examples include a radio, such as the Texas Instruments CC2530. Alternatives include ARM processors and very low power DSPs such as the Belasigna 300 by On Semiconductor or other processors designed for Bluetooth headsets. Accordingly, the processor 38 may be an 8-bit or 16-bit processor, while the processor of the monitor 12 may be a 32-bit or 64-bit processor, such as those used in monitors available from Nellcor.

Random access memory (RAM) 42 and/or non-volatile (NV) memory 44 may be connected to the system bus 40. The RAM 42 may be implemented using low-power memory modules, and may be 8-bit or 16-bit addressable for use with an 8-bit or 16-bit processor 38. In certain embodiments, the RAM 42 may be implemented as a memory that is part of the processor 38, or RAM 42 may be a designated portion of NV memory 44. NV memory 44 may be an EEPROM or flash memory storage device. In the illustrated embodiment, the processor 38, RAM 42, and NV memory 44 are incorporated into processing circuitry 45. That is, in certain implementations, the processor 38, RAM 42, and/or NV memory 44 may be included within a single chip within the sensor 14. Indeed, in certain embodiments, the processing circuitry 45 may also include the system bus 40, TPU 46, the A/D 56, the QSM 58, and/or the wireless modules 18 within a single chip.

In an embodiment, NV memory 44 may include one or more sets of instructions to be executed by the processor 38 for carrying out the techniques described herein. That is, based at least in part on the signals provided by the detector 26, the microprocessor 38 may calculate a physiological parameter of interest using various algorithms and coefficient values that may be stored in NV memory 44. Additionally, NV memory 66 and/or RAM 42 may also store historical data and/or values (e.g., detector signal data, data points, trend information) for the physiological parameter of the patient. For example, the NV memory 44 and/or RAM 42 may store calculated SpO$_2$ values (e.g., one value per minute) for the most recent twenty minutes of sensor operation. These stored values may be used by the processor 38 to determine the variance in a patient physiological parameter (e.g., SpO$_2$), as discussed in greater detail below. By further example, NV memory 66 and/or RAM 42 may be used to temporarily store or buffer the detector signal data and/or calculated physiological parameter values for a period of time, such as if the wireless connection 20 is interrupted. Accordingly, upon reestablishing wireless communications, the sensor 14 may send the buffered data to the monitor 12 in a quick burst before resuming normal operations. A similar buffer mechanism may also be employed, for example, if the processor 38 is temporarily lagging behind on detector signal data processing. In such circumstances, when the processor 38 becomes available, or when the patient sensor 14 transfers the data to the monitor 12 for processing, the detector signal data may be appropriately processed without resulting a gap in patient's physiological data.

The algorithms stored in NV memory 44 may be used to determine the physiological parameter of the patient using the low-power processor 38 of the wireless patient sensor 14. These algorithms may include those disclosed in U.S. Pat. No. 4,911,167, filed Mar. 30, 1988, U.S. Pat. No. 6,411,833, filed Nov. 5, 1999, and the Proceedings of the 28$^{th}$ IEEE EMBS Annual International Conference (2006) entitled "INVESTIGATION OF SIGNAL PROCESSING ALGORITHMS FOR AN EMBEDDED MICROCONTROLLER-BASED WEARABLE PULSE OXIMETER," which are all incorporated by reference herein in their entirety. For example, in the case of a pulse oximetry patient monitoring system 10, NV memory 44 may include algorithms that calculate a SpO$_2$ value using a ratio-of-ratios calculation, in which the SpO$_2$ value is equal to the ratio of the time-variant (AC) and the time-invariant (DC) components of the detector signal acquired using RED light divided by the ratio of the AC and DC components of the detector signal acquired using IR light. In general, a number of processing algorithms may be used to determine the AC and DC components of the detector signal. For example, the DC components of the detector signals may be determined using a number of different methods, including a moving average over a defined time window, an infinite impulse response (IIR) Butterworth low-pass filter, or using a minimum plethysmograph value over a defined time window. Furthermore, for such a calculation, the AC component may be determined using a number of different methods, such as using an average of local plethysmograph derivatives over a period of time, using a derivative-base peak identification and subsequently determining the difference between the amplitude and nadir of each pulse, using a difference in the maximum and minimum values of the plethysmograph waveform over a period of time, and/or using a fast Fourier transform (FFT) with subsequent amplitude analysis. It should be noted that the aforementioned processing algorithms are provided as examples, and patient monitoring system 10 may utilize any number of algorithms as would be known to one of ordinary skill in the art. It should be further noted that certain algorithms may afford differences in computational cost, making certain algorithms more fitting for the low-power processor 38 of the wireless patient sensor 14 and others more fitting for the processor of the patient monitor 12. For example, using a difference in the maximum and minimum values of the plethysmograph waveform over a period of time to determine the AC component of a detector signal may have significantly lower computational cost than using a fast Fourier transform (FFT) with subsequent amplitude analysis to do the same. Accordingly, the first algorithm may be implemented by the wireless patient sensor 14 while the second may be implemented by the patient monitor 12.

Additionally, NV memory 44 may store caregiver preferences, patient information, and various operational parameters of the wireless patient sensor 14. For example, the NV memory 44 may store information regarding the wavelength of one or more light sources of the emitter 24, which may allow for selection of appropriate calibration coefficients for calculating a physiological parameter (e.g., blood oxygen saturation). Furthermore, in an embodiment, these calibration coefficients and/or calibration curves may also be stored in the NV memory 44 after they have been determined through empirical calibration of the sensor 14 during or after manufacturing. Additionally, in circumstances where the monitor 12 will be calculating the physiological parameter of the patient 30, NV memory 44 may also provide information regarding the emitter wavelengths, calibration coefficients, and/or calibration curves to the patient monitor 12 via the wireless connection 20.

A time processing unit (TPU) 46 may provide timing control signals to light drive circuitry 48 to control when the emitter 24 is illuminated, and if multiple light sources are used, the multiplexed timing for the different light sources. The TPU 46 may optionally also control the gating-in of signals from the detector 26 through an amplifier 50 and a switch 52. In embodiments where multiple light sources are used, the switch 52 may ensure that signals are sampled at the proper time, depending upon which of the multiple light sources is illuminated. After passing through the switch 52 and a subsequent amplifier 54, the signal may pass through an analog-to-digital converter 56 before arriving at the queued serial module (QSM) 58. The digitized detector signal may be collected and temporarily stored in the QSM 58 for later downloading into RAM 42 as the QSM 58 fill up. In an alternative embodiment, the processor 38 may receive the digitized detector signal directly from the A/D converter 56, without the use of a QSM 58, and transfer it to RAM 42 for processing The processor may also use a built-in Direct Memory Access (DMA) peripheral to perform the data transfer in the background while the core is in a low-power or sleep mode, or while the core is processing previously received A/D samples.

In RAM 42, the digitized detector signal may be divided into portions and stored or encoded in such a way to include details regarding the detector signal and/or the detector signal acquisition. In certain embodiments, the digitized detector signal may be divided into portions and stored in RAM 42 based on the wavelength of light emitted when acquiring the detector signal. For example, a portion of a digitized detector signal may be stored in RAM 42 along with data indicating that the signal was acquired when the emitter 24 was emitting a particular wavelength of light (e.g., RED or IR) into the tissue of the patient 30. Alternatively, in certain embodiments, the digitized detector signal may include a continuous stream of detector signals acquired using two or more wavelengths of light (e.g., RED and IR). In such embodiments, a set of timing data, representing the activities of the TPU 46, light drive 48, and/or emitter 24 during detector signal acquisition, may be stored in RAM 42 so that a processor (e.g., processor 38) may use this timing data to deconvolute the digitized detector signal into the component detector signals for each wavelength emitted. Accordingly, when the detector signal data is subsequently processed by the processor 38 of the wireless patient sensor 14, or by the processor of the patient monitor 12, the included signal acquisition details may ensure that appropriate portions of the digitized detector signal are used in the appropriate point in the calculation when determining the physiological parameter of the patient 30. As such, for clarity, the term "detector signal data" is used herein to describe the digitized detector signal or filtered detector signal combined with any other signal acquisition details that may be used to interpret the digital detector signal. For example, the detector signal data may, in addition to a digitized detector signal, incorporate emitter wavelength information, timing data, calibration coefficients, or calibration curves that may be used by a processor (e.g., processor 38) to process the digitized detector signal and/or calculate the physiological parameter of the patient 30.

Once the detector signal data has been stored in RAM 42, it may be further processed by the processor 38 of the wireless patient sensor 14 to determine specific patient physiological parameters of interest, such as pulse rate, blood oxygen saturation, and so forth. The calculated physiological parameter of the patient may be significantly smaller in size (i.e., fewer bits of information) than the raw data. For example, a raw 16-bit digital stream of photoplethysmographic data of between approximately 50 Hz or less to 2000 Hz or more (e.g., approximately 1211 Hz) may be sampled down to between approximately 10 Hz to 200 Hz (e.g., approximately 57.5 Hz), before being processed to obtain an instantaneous pulse rate at a given time, which may occupy only about 8 bits. By further example, the pulse rate of a patient may be calculated once per 1211 raw samples at 16-bits for RED and IR light each second, resulting in 2422 bytes of data per second. In contrast, a single byte may be used to transmit either a heart rate or $SpO_2$ value. In this example, the amount of raw data that would be transmitted in 10 seconds would be 24220 bytes, and the amount of data that would be transmitted to update the calculated heart rate and $SpO_2$ values once every 5 seconds would be 4 bytes. That is, in this example, the wireless module 18 may be activated approximately 6000 times longer in order to transmit raw data than would be used to transmit the corresponding calculated parameter values.

As such, transferring detector signal data over the wireless communication link 20 costs considerably more bandwidth and battery power than does transferring the calculated physiological parameter of the patient 30. However, in situations where the digitized detector signal is noisy, complex, or representative of a complex event in the patient 30, it may be desirable to have the more powerful processing circuitry of the patient monitor 12 handle the signal processing and physiological parameter calculation. In such situations, the detector signal data may be transferred wirelessly despite the associated bandwidth and battery power cost. The raw (or preprocessed) data may also be sent over a wireless link 20 for a short time for display purposes if requested by the operator (e.g. through a button press on the patient monitor 12) so they may evaluate the signal quality or determine suitable placement of the sensor.

Figure 3:
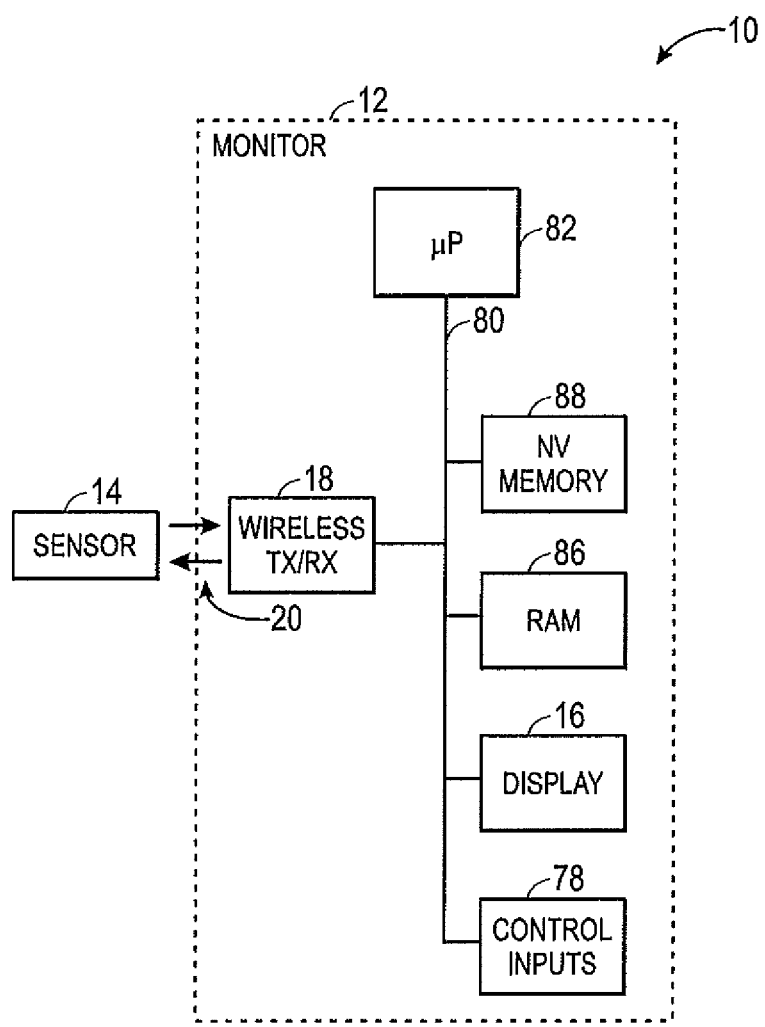
FIG. 3 is a block diagram of the patient monitor of FIG. 1, in accordance with an embodiment.

As previously mentioned, the patient monitor 12 may, at times, receive a sensor-calculated value for the physiological parameter of the patient 30 and, at times, receive detector signal data to calculate the physiological parameter of the patient 30. As illustrated in FIG. 3, the patient monitor 12 of the patient monitoring system 10 accordingly includes circuitry for signal processing, such as may be found in Nellcor OxiMax N-600x pulse oximeters. In the illustrated embodiment, the patient monitor 12 includes a display 16 to present information about the patient 30 and the patient monitoring system 10. Additionally, the monitor 12 includes a plurality of control inputs 78 that enable an operator to adjust the settings of the patient monitoring system 10. The microprocessor 82 of the monitor 12 is coupled to the main system bus 80 and generally controls the operation of the monitor 12. The processor 82 may work in conjunction with RAM 86 and NV memory 88 to determine the physiological parameter of the patient 30.

The patient monitor 12 also includes a wireless module 18 coupled to the main bus 80 and controlled by the processor 82. The wireless module 18 facilitates wireless communication of data and instructions between the patient monitor 12 and the patient sensor 14. For example, the wireless module 18 of the monitor 12 may receive data such as calculated physiological parameter value or digitized detector signals from the wireless patient sensor 14. By further example, the patient monitor 12 may send instructions to the wireless patient sensor 14, via wireless module 18, to stop calculating the physiological parameter of the patient 30 and forward the detector signal data to the monitor 12 for processing, as set forth in detail below.

In general, when data is received from the wireless patient sensor 14, the patient monitor 12 may determine which type of data has been received. As such, data received from the patient sensor 14 may be stored in RAM 86 so that the processor 82 may examine the received data to determine whether it is a sensor-calculated physiological parameter value or detector signal data. For example, the processor 82 may determine that received data contains a sensor-calculated value for the physiological parameter of the patient 30. Accordingly, the monitor 12 may present the sensor-calculated physiological parameter value on display 16 and may store the value in NV memory 88, along with other historical physiological parameter values, for future comparisons and/or trend analysis. Alternatively, the processor 82 may determine that the received data contains detector signal data to be processed by the processor 82 to determine the physiological parameter of the patient 30. Accordingly, the processor 82 of the monitor 12 may extract the digitized detector signal, along with any other signal acquisition details pertinent to performing signal processing and/or to determining the physiological parameter value, from the detector signal data so that the processor 82 may process the digitized detector signal and determine the physiological parameter of the patient 30.

Figure 4:
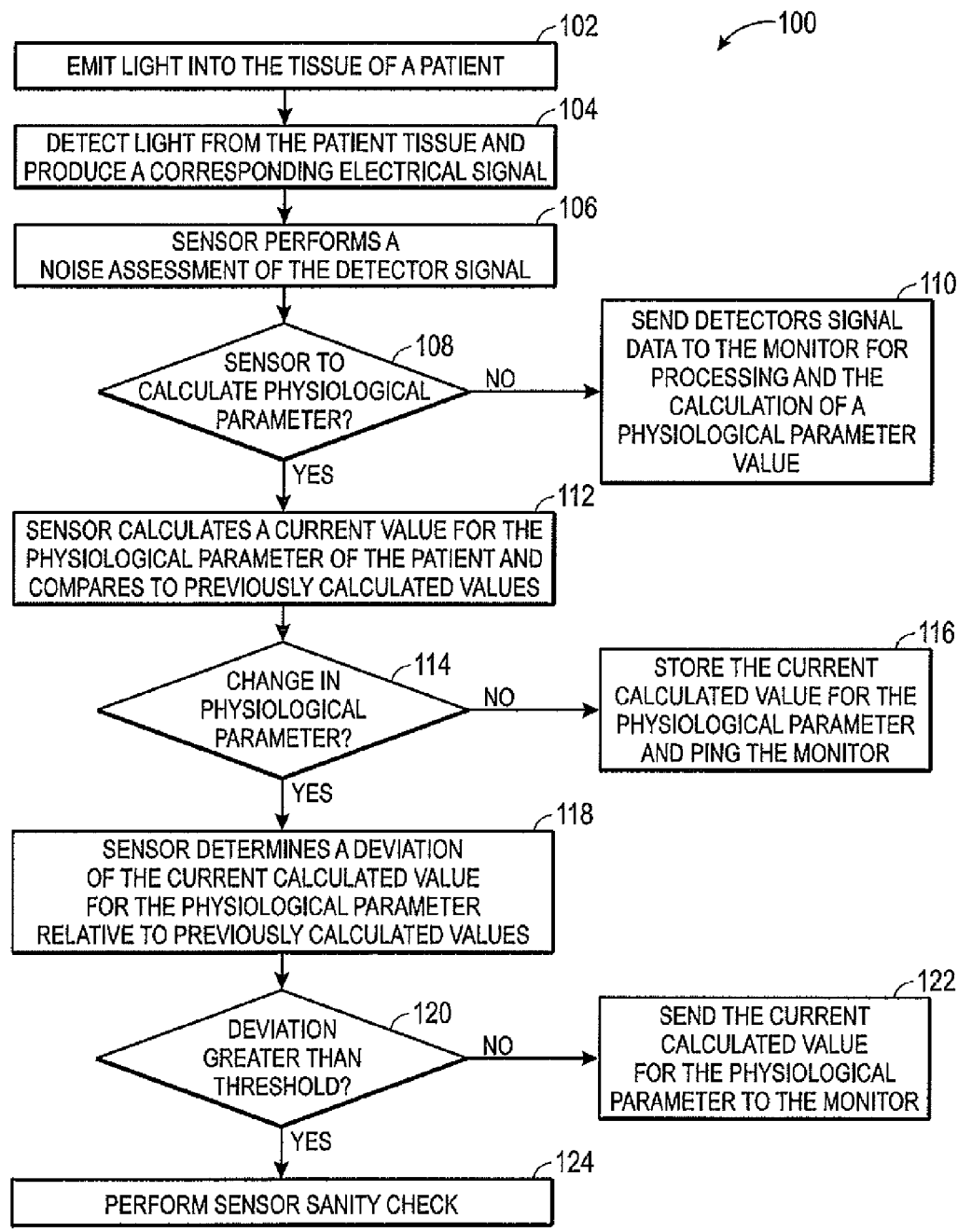
FIG. 4 is a flowchart illustrating a process for determining whether detector signal data is to be processed by the wireless patient sensor or the patient monitor, in accordance with an embodiment.

To determine when the detector signal data is to be processed by the wireless patient sensor 14 and when it is to be sent to the monitor 12 for processing, the patient monitoring system 10 may determine if the digitized detector signal is noisy, complex, rapidly changing, highly variable and/or the result of a complex event in the patient. For example, FIG. 4 illustrates a high-level block diagram of an embodiment of a process by which the wireless patient sensor 14 may make such determinations, although it should be understood that the sensor 14 may make these determinations alone or in any combination with the patient monitor 12. The process 100 begins with the wireless patient sensor 14 driving the emitter 24 (e.g., using the light drive 48) to emit light into the tissue of a patient 30 (block 102). For example, the emitter 24 may be configured to emit light of two different wavelengths (e.g., RED and IR) based upon timing signals provided by the TPU 46 via the light drive 48. Then, the detector 26 of the sensor 14 detects the light from the tissue of the patient 30 and produces a corresponding electrical signal (block 104).

If the detector signal is noisy, the simplified processing of the sensor 14 may be insufficient to calculate an accurate value for the physiological parameter, thus the use of the more robust processing capabilities of the monitor 12 may be warranted. Hence, the wireless patient sensor 14 may perform signal a noise assessment of the detector signal (block 106). For example, the noise assessment may be performed according to the process illustrated in FIG. 5, as described in detail below. The wireless patient sensor 14 may then, based upon this noise assessment, decide if the sensor 14 is to calculate the physiological parameter of the patient 30 (block 108). For example, if the sensor 14 determines in block 106 that the digitized detector signal is noisy, the sensor 14 may send the detector signal data to the patient monitor 12 for processing and for the calculation of the physiological parameter of the patient 30 (block 110).

Otherwise, the wireless patient sensor 14 may calculate the physiological parameter of the patient 30 and compare the calculated value to previously calculated values for the physiological parameter (block 112). The sensor 14 may make the comparison since significant changes in the calculated values could be indicative of a complex detector signal (e.g., the complex event could be the result of noise or the patient 30 experiencing a cardiac arrhythmia). In such circumstances, more careful processing of the detector signal data may be warranted, and the patient sensor 14 may not determine the cause of the rapid change of high variability of the signal before determining that the simplified processing of the sensor 14 is insufficient and that the monitor 12 should process the detector signal data. In the case of a pulse oximetry monitoring system 10, the processor 38 of the sensor 14 may use digitized detector signals acquired using RED and IR light, in combination with calibration coefficients and algorithms stored in NV memory 44, to determine an instantaneous value for the patient's pulse rate and oxygen saturation (e.g., $SpO_2$ value). For example, the patient's pulse rate may be determined to be 60 bpm, and the patient's $SpO_2$ value may be determined to be 98%. Then, the processor 38 of the sensor 14 may compare the calculated pulse rate and $SpO_2$ values to values previously calculated by the sensor 14 (e.g., stored in NV memory 44). It should be noted that, in certain embodiments, if the sensor 14 is unable to determine a value for the physiological parameter within an acceptable time frame (e.g., a time-out), the sensor 14 may send the detector signal data, along with any additional detector signal data that may have been collected during the time frame, to the patient monitor 12 for processing.

In comparing the calculated values, the wireless patient sensor 14 determines whether there has been a change in the value of the physiological parameter since it was last reported to the patient monitor 12 (block 114). For this, the processor 38 of the sensor 14 may specifically compare the current calculated value for the physiological parameter to the previously calculated physiological parameter value. In certain embodiments, the processor 38 of the sensor 14 may only consider the value to have changed if the difference between the current and previous values is greater than a threshold value (e.g., stored in NV memory 44). For example, if the previously calculated $SpO_2$ value was 97.6%, the current value is 97.8%, and the threshold value is 0.5%, the processor 38 of the sensor 14 may determine that the value has not changed. In certain embodiments, the threshold value may be set by the operator on the patient monitor 12, and communicated to the patient monitor 12, via the wireless connection 20, where it may be stored in NV memory 44.

Accordingly, if the processor 38 of the wireless patient sensor 14 determines that physiological parameter has not changed, the processor 38 may store the calculated value (e.g., in NV memory 44) for future comparisons and may ping the monitor 12 (block 116). That is, since the sensor 14 does not have a different physiological parameter value to deliver to the monitor 12, the sensor 14 may instead send a minimal amount of information (i.e., a ping) to the patient monitor 12 to verify that the wireless patient sensor 14 is still active and that there is no change in the physiological parameter value to display. In certain embodiments, since the calculated physiological parameter may only be a few bits (e.g., 8-16 bits) in size, the patient sensor 14 may send the calculated value to the monitor 12 in lieu of the ping. Regardless, a minimal amount of wireless communication may be performed between the sensor 14 and the monitor 12 to minimize battery consumption in the sensor 14 and minimize wireless network congestion.

Alternatively, if the processor 38 of the wireless patient sensor 14 determines that there has been a change in the value of the physiological parameter (block 114), the processor 38 of the sensor 14 may then determine a deviation or variance of the current calculated physiological parameter value relative to historical values that were previously calculated by the sensor 14 (block 118). For example, the processor 38 may compare the most recently computed physiological parameter value to any number of previously computed values. In general, the processor 38 of the sensor 14 may compare the collection of computed values to determine how much the physiological parameter has varied over time. For example, the processor 38 of the sensor 14 may perform a variance, standard deviation, and/or root mean square deviation calculation on the current value relative to the trend of the historical values. Alternatively, in certain embodiments, the sensor 14 may send the current calculated physiological parameter value directly to the patient monitor 12 after calculation, and the patient monitor 12 may instead perform the variance, standard deviation, and/or root mean square deviation calculation on the current calculated physiological parameter value relative to a trend of the historical values (e.g., stored in NV memory 88) calculated by either the sensor 14 or the monitor 12.

Then, the processor 38 may decide whether the deviation or variance of the current value is greater than a particular threshold (block 120). For example, the processor 38 may calculate the standard deviation using any number of previous calculated values (e.g., stored in NV memory 44) and then determine if the deviation of the current value is beyond a particular threshold value. In certain embodiments, the threshold value may be set by the operator on the patient monitor 12 (e.g., using display 16 and control inputs 78) and communicated to the patient monitor 12, via the wireless connection 20, where it may be stored in NV memory 44. For example, the threshold value may indicate that a calculated physiological parameter value that deviates by one standard deviation or less relative to the historical data is acceptable and should be sent to the patient monitor 12 (block 122).

However, if the deviation of the current value is greater than the threshold value, this may be the result of a complex detector signal or a complex physiological event in the patient 30, e.g., a rapid desaturation caused by a severe condition such as a pulmonary embolism or a condition such as sleep apnea. In either case, the patient monitor 12 may perform a sanity check to determine if the patient sensor 14 is properly calculating the physiological parameter (block 124). That is, if the currently calculated value for the physiological parameter deviates greatly from the trend of previously calculated values, this may mean that the simplified signal processing and physiological parameter calculation algorithms that the wireless patient sensor 14 utilizes may not be as well-suited for the current calculation as the internal components of the patient monitor 12. As such, a deviation of the current calculated physiological parameter value beyond the threshold value will result in the sensor 14 transmitting both the current calculated value for the physiological parameter and the corresponding detector signal data to the monitor 12 as part of the sanity check process described in detail below.

Figure 5:
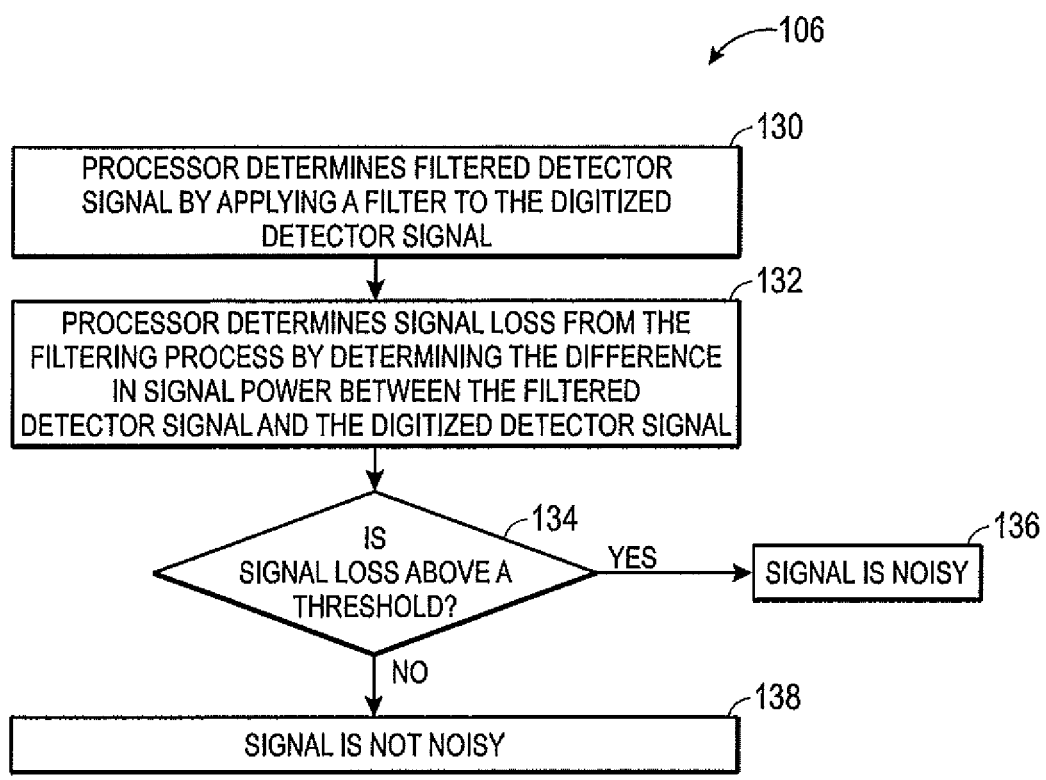
FIG. 5 is a flowchart illustrating a process for determining whether a detector signal is noisy, in accordance with an embodiment.

As mentioned with respect to the process 100, the processor 38 of the wireless patient sensor 14 performs a noise assessment of the detector signal (block 106). In general, the noise assessment may determine if a substantial portion of the signal power is in a standard frequency range for pulse oximetry measurements (e.g., between approximately 0.1 and 5 Hz). By way of example, FIG. 5 illustrates an embodiment of a process 106 that the sensor 14 may use to perform a noise assessment. This process 120 may begin with the processor 38 determining a filtered detector signal by applying of one or more filter operations to the digitized detector signal (block 130). For example, the processor 38 may perform a low-pass filter operation on the digitized detector signal by subtracting signals above a particular frequency threshold. In another embodiment, the filter operation may include a different type of filtering (e.g., a high-pass filter), plurality of filters in combination, and/or a noise reduction algorithm. The filtered detector signal may be stored in RAM 42 separately from the digitized detector signal for comparison. Next, the processor 38 may determine the signal loss (e.g., the loss of total signal intensity) from the filtering operation by determining the difference in the signal power of the filtered detector signal and the digitized detector signal (block 134). For example, the processor 38 may determine a value for the power of the digitized detector signal, p1, as the sum of square of the plethysmograph signal over a period of time. The processor 38 may also determine a value for the power of the filtered detector signal, p2, as the sum of square of the filtered plethysmograph signal over a period of time. Then, the processor 38 may use the ratio of p2 to p1 to determine the signal loss of the filtering operation.

If the signal loss is greater than a threshold value (e.g., stored in NV memory 44) (block 134), the detector signal may be determined to be noisy (block 136). In certain embodiments, the threshold value may be set by the operator on the patient monitor 12 and communicated to the patient monitor 12 via the wireless connection 20. For example, the threshold value may be 20% and, accordingly, a signal loss greater than 20% from the filter operation would indicate a noisy detector signal. However, if the signal loss from the filter operation is less than the threshold value, the detector signal may be considered to not be noisy (block 138).

Figure 6:
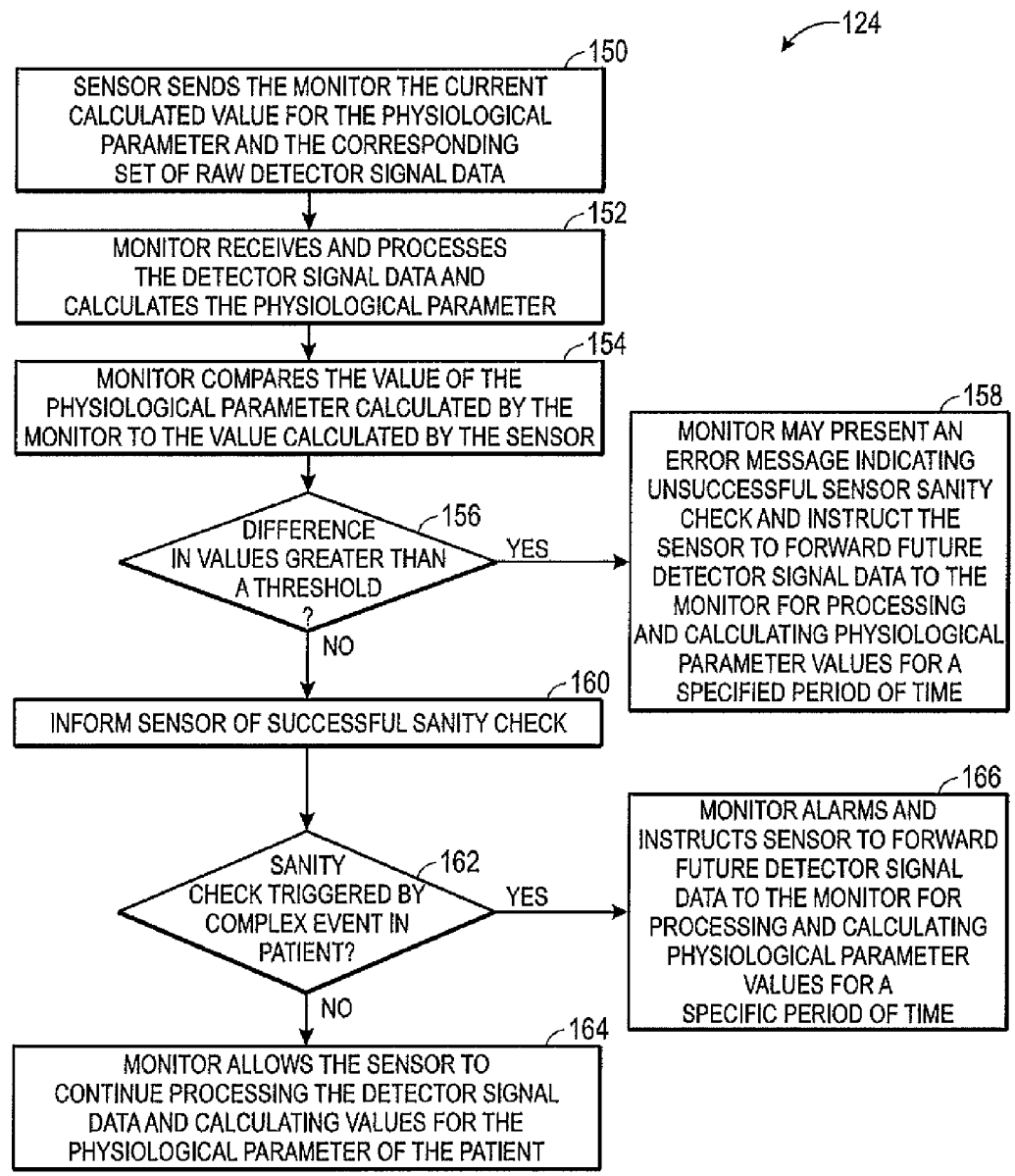
FIG. 6 is a flowchart illustrating a process for performing a sanity check of the wireless patient sensor system, in accordance with an embodiment.

As also mentioned above with regard to the process 100, a deviation of the current calculated physiological parameter value beyond the threshold value may result in the sensor 14 performing a sanity check (block 124). An embodiment of the sanity check process 124 is illustrated in FIG. 6. The process 124 may begin with the wireless patient sensor 14 sending the current calculated value for the physiological parameter, as well as the corresponding detector signal data, to the patient monitor 12 (block 150). It should be noted that, in certain embodiments, the patient monitor 12 may additionally or alternatively request any stored or buffered calculated physiological parameter values and detector signal data rather than the most recent. That is, in certain embodiments, the patient monitor 12 may request and receive any historical detector signal data and/or sensor-calculated physiological parameter values (e.g., stored in RAM 42 and/or NV memory 44) to present on the display 16 and/or to verify the performance of the sensor 14.

The patient monitor 12 subsequently receives and processes the detector signal data and calculates the physiological parameter of the patient 30 (block 152). Once the detector signal data has been received and is stored in RAM 86, it may be further processed by the processor 82. For example, the processor 82 may perform complex signal processing and/or noise correction algorithms on the detector signal data that are beyond the computational power of the processor 38 of the sensor 14. Finally, the processor 82 of the monitor 12 performs the calculation of the physiological parameter. Here again, the processor 82 may utilize algorithms in the calculation of the physiological parameter of the patient 30 that are beyond the processing power of the processing circuitry of the patient sensor 14.

The patient monitor 12 may then compare (block 154) the monitor-calculated value for the physiological parameter to the sensor-calculated value in order to the determine if the difference between the two values is greater than a threshold value (e.g., stored in NV memory 88) (block 156). That is, since the algorithms used by the wireless patient sensor 14 and the patient monitor 12 to calculate the physiological parameter may be different, a difference between the two values is only a concern if it exceeds a threshold value. In certain embodiments, this threshold value may be set by the operator on the patient monitor 12 (e.g., using the display 16 and the control inputs 78) and stored in NV memory 88 for said comparisons.

If the difference in the values for the patient physiological parameter calculated by the wireless patient sensor 14 and the patient monitor 12 are determined to be different, the monitor 12 may present an error message (e.g., on display 16) indicating that an unsuccessful sanity check has occurred or until the event or complex signal subsides (block 158). While such an event may be indicative of a fault in the sensor 14, it may also be the result of a complex detector signal. That is, the simplified algorithms of the sensor 14 may be best equipped to handle typical signal processing and calculation of patient physiological parameters within normal or expected bounds; however, the patient monitor 12 may be more adept to perform the signal processing and/or physiological parameter calculation for complex detector signal data. For example, a pulse oximetry sensor 14 may be configured to determine the pulse rate of a patient and, accordingly, be equipped with a low-power processor and simplified algorithms to process the detector signal data. However, a patient 30 experiencing an arrhythmia may produce a complex detector signal that may be better processed by the patient monitor 12. By further example, the detector signal data may include difficult to detect, low-frequency noise that may not have been detected by the sensor 14 (e.g., in block 106) and, therefore, may result in a complex detector signal data that the monitor 12 may be more adept to process.

Accordingly, the patient monitor 12 may also send a message to the wireless patient sensor 14 instructing it to forward the future detector signal data to the monitor 12 for processing for a specified amount of time (block 158). Accordingly, in an embodiment, the wireless patient sensor 14 may not process the signal or calculate the physiological parameter during this time period in order to conserve power while wirelessly forwarding the detector signal data to the monitor 12 for processing and physiological parameter calculation. In certain embodiments, once the period of time has passed, the sensor 14 may successfully repeat the sanity check process 124 before resuming processing of the detector signal data.

However, if the difference in the values for the patient physiological parameter calculated by the wireless patient sensor 14 and the patient monitor 12 are determined not to be different, the monitor 12 may inform the sensor 14 of a successful sanity check (block 160). That is, the monitor 12 may confirm that the sensor 14 has properly calculated the value of the physiological parameter. As such, one possibility for the deviation in the sensor-calculated value that triggered the sanity check (e.g., in block 120) is that the sensor 14 properly calculated the physiological parameter during a complex physiological event within the patient. For example, the sensor 14 may determine that a patient's pulse rate and oxygen saturation values are rapidly changing because the patient is suffering from a seizure, sleep apnea, heart attack, or similar complex physiological event occurring in the patient 30. While the successful sanity check indicates that the sensor 14 may be capable of calculating the physiological parameter, the complex physiological event may approach, and eventually surpass, the limit of the processing power of the sensor 14. Furthermore, in the case of a complex physiological event in the patient 30, it may be more important to have the more powerful processing circuitry and more precise algorithms of the monitor 12 calculate the physiological parameters of the patient 30 than to conserve the battery 34 of the sensor 14 or to reduce wireless congestion during the event.

Accordingly, the patient monitor 12 may determine if the sanity check was triggered by a complex physiological event in the patient (block 162). To do this, the patient monitor 12 may perform an evaluation of the detector signal data received from the wireless patient sensor 14. Additionally, the patient monitor 12 may evaluate the current calculated value and previously calculated physiological parameter values (e.g., calculated by either the monitor 12 or the sensor 14 and stored in NV memory 88) to identify trends in the data that are indicative of a complex physiological event in the patient. For example, the processor 82 of the patient monitor 12 may use an algorithm (e.g., stored in NV memory 88) to analyze calculated $SpO_2$ values of the patient and determine if the patient 30 is experiencing apnea, which may be expressed in steadily falling oxygen saturation values.

If the patient monitor 12 determines that a complex physiological even is not occurring in the patient 30, the monitor 12 may allow the wireless patient sensor 14 to continue calculating physiological parameter values for the patient 30 (block 164). If, however, the monitor 12 determines that a complex physiological event is occurring in the patient 30, the monitor 12 may alarm to inform a medical professional of the complex event in the patient 30 and instruct the wireless patient sensor 14 to forward future detector signal data to the patient monitor 12 for processing for a specified period of time (block 166). As such, in certain embodiments, the wireless patient sensor 14 may not process the signal or calculate the physiological parameter during this time period in order to conserve power while wirelessly forwarding the detector signal data to the monitor 12 for processing and physiological parameter calculation. In an embodiment, the monitor 12 may indicate the amount of time that it will process data based, at least in part, on a specific event detected in the physiological parameter of the patient 30. For example, if the patient monitor 12 determines that the sanity check is triggered by an sleep apnea event that the patient 30 only occurs for a few seconds every hour (e.g., based upon physiological trend data stored in NV memory 88), the monitor 12 may indicate that it will continue to process the detector signal data for a short period of time (e.g., less than 30 sec) after such an event has been detected. By further example, if the monitor 12 determines that the patient is experiencing a critical complex physiological event (e.g., respiratory failure, heart attack, seizure, etc.) the monitor 12 may indicate that it will process the detector signal data for a longer period of time (e.g., several minutes to hours) after such an event has been detected. In certain embodiments, once the period of time has passed, the sensor 14 may successfully repeat the sanity check process 124 before resuming processing of the detector signal data. Additionally, it should be noted that, while a sanity check may be triggered by the events described above, in certain embodiments, an operator may request a sanity check to be performed in order to manually verify the performance of the patient monitoring system 10. Furthermore, in certain embodiments, the operator may request, in addition to or in the alternative to a sanity check, that a portion of the detector signal data be presented on the display 16 for visual inspection by the operator.

Accordingly, using the techniques described herein, a wireless patient sensor 14 may limit the amount of data transmitted to the patient monitor 12 and, thereby, improve the life of the battery 34 of the sensor 14 and reduce interference and congestion in the wireless spectrum. The disclosed techniques afford the greatest improvement in circumstances where the physiological parameter of interest is simple and relatively static. For example, the disclosed embodiments would provide a significant power savings in situations where a patient's physiological parameter does not vary greatly over time, such as may occur when a patient is asleep for an extended period of time.

What is claimed is:

1. A patient sensor device, comprising:
   an emitter configured to emit light into a tissue of a patient;
   a detector configured to detect the light from the tissue of the patient and produce a corresponding electrical signal;
   signal processing circuitry configured to receive and convert the electrical signal of the detector into detector signal data;
   a wireless module communicatively coupled to a patient monitor and configured to transmit a physiological parameter value, the detector signal data, or both, to the patient monitor; and
   a processor configured to:
   determine whether the patient sensor or the patient monitor should calculate the physiological parameter value based, at least in part, on the detector signal data;
   calculate the physiological parameter value for the patient based, at least in part, on the detector signal data, if the processor determines that the patient sensor should calculate the physiological parameter value; and
   send the detector signal data to the patient monitor, via the wireless module, to calculate the physiological parameter value for the patient based, at least in part, on the detector signal data, if the processor determines that the patient monitor should calculate the physiological parameter value.

2. The patient sensor of claim 1, wherein the processor determines that the detector signal data is noisy by applying a filter to the detector signal data, and if a signal loss from the application of the filter is greater than a threshold value, then the detector signal data is determined to be noisy.

3. The patient sensor of claim 1, wherein the processor is further configured to determine if the calculated physiological parameter value is different from a previously calculated physiological parameter value, and if it is not, to store the calculated physiological parameter value and inform the patient monitor, via the wireless module, that the physiological parameter value has not changed.

4. The patient sensor of claim 1, wherein the processor is further configured to determine if a deviation of the calculated physiological parameter value, relative to a plurality of previously calculated physiological parameter values, is greater than a threshold value, and if it is not, to send the calculated physiological parameter value to the patient monitor.

5. The patient sensor of claim 4, wherein the processor is further configured to supply the calculated physiological parameter value and the detector signal data to the patient monitor, via the wireless module, if the processor determines that the deviation of the calculated physiological parameter value is greater than the threshold value.

6. The patient sensor of claim 1, wherein the processor is further configured to determine if the patient monitor or the patient sensor should calculate the physiological parameter based, at least in part, on instructions from the patient monitor.

7. A patient monitor, comprising:
   a display configured to present a physiological parameter of a patient;
   a wireless module configured to receive a sensor-calculated physiological parameter value, corresponding detector signal data, or both, from a wireless patient sensor;
   a processor configured to:
   instruct the display to present the sensor-calculated physiological parameter value when the corresponding detector signal data is not received from the wireless patient sensor; and
   determine a monitor-calculated physiological parameter value when the corresponding detector signal data is received from the wireless patient sensor and instruct the display to present the monitor-calculated physiological parameter value.

8. The patient monitor of claim 7, wherein the processor is further configured to compare the sensor-calculated physiological parameter value to the monitor-calculated physiological parameter value when both the sensor-calculated physiological parameter value and the corresponding detector signal data are received by the wireless module.

9. The patient monitor of claim 8, wherein if the difference between the sensor-calculated physiological parameter value and the monitor-calculated physiological parameter value is greater than a threshold value, the processor is configured to instruct the wireless patient sensor, via the wireless module, to:
   send subsequent detector signal data to the patient monitor to determine subsequent monitor-calculated physiological parameter values for a period of time; and
   postpone determining subsequent sensor-calculated physiological parameter values for the period of time.

10. The patient monitor of claim 7, wherein the processor is further configured to determine if the corresponding detector signal data includes a complex physiological event based, at least in part, on previous sensor-calculated physiological parameter values, previous monitor-calculated physiological parameter values, or both.

11. The patient monitor of claim 10, wherein, if the processor determines that the corresponding detector signal data includes a complex physiological event, the processor is configured to instruct the wireless patient sensor, via the wireless module, to:
   send subsequent detector signal data to the patient monitor to determine subsequent monitor-calculated physiological parameter values for a period of time; and
   postpone determining subsequent sensor-calculated physiological parameter values for the period of time.

12. The patient monitor of claim 7, wherein the processor is further configured to request and receive detector signal data from the patient sensor, via the wireless module, and to display the detector signal data on the display.

13. A method, comprising:
   collecting detector signal data from a detector of a wireless patient sensor;
   determining, via the wireless patient sensor, if the detector signal data is noisy or complex;
   calculating, via the wireless patient sensor, a value for a physiological parameter of the patient based, at least in part, on the detector signal data when the detector signal data is not noisy;
   sending the calculated value for the physiological parameter from the wireless patient sensor to a patient monitor when the value for the physiological parameter is calculated by the wireless patient sensor;

sending the detector signal data to the patient monitor when the detector signal data is noisy or complex or when the detector signal data is requested by the patient monitor; and calculating, via the patient monitor, a value for a physiological parameter of the patient based, at least in part, on the detector signal data when the detector signal data is received from the wireless patient sensor.

14. The method of claim 13, wherein determining if the detector signal data is noisy further comprises determining a signal power difference between filtered detector signal data and the detector signal data, and the detector signal data is determined to be noisy if the signal power difference is greater than a threshold value.

15. The method of claim 14, wherein the filtered detector signal is produced via the application of a low-pass filter, a high-pass filter, a noise filter, or any combination thereof, to the detector signal data.

16. The method of claim 13, wherein sending the calculated value for the physiological parameter to the patient monitor further comprises determining if the calculated value for the physiological parameter is different than a previously calculated value for the physiological parameter and, if they are determined to be different, sending the calculated value for the physiological parameter to the patient monitor.

17. The method of claim 16, comprising storing the calculated physiological value in the patient sensor and sending a minimal amount of data to inform the patient monitor that the physiological parameter has not changed, if the calculated value for the physiological parameter and the previously calculated value for the physiological parameter are determined to be equivalent.

18. The method of claim 13, comprising determining, via the wireless patient sensor, a deviation of the calculated value for the physiological parameter, relative to previously calculated values for the physiological parameter, and if the deviation is greater than a threshold value, then the detector signal data is determined to be complex.

19. The method of claim 13, comprising determining, via the patient monitor, a deviation of the calculated value for the physiological parameter, relative to previously calculated values for the physiological parameter, and if the deviation is greater than a threshold value, then the detector signal data is determined to be complex.

20. The method of claim 13, comprising:

determine, via the patient monitor, if the corresponding detector signal data includes a complex physiological event in the patient, and if it does, instructing the wireless patient sensor to:
send subsequent detector signal data to the patient monitor to calculate subsequent values for the physiological parameter for a period of time; and
postpone determining subsequent values for the physiological parameter values for the period of time.

* * * * *